United States Patent [19]

Brodard

[11] Patent Number: 4,919,139

[45] Date of Patent: Apr. 24, 1990

[54] ELECTRICAL NEUROMUSCULAR STIMULATION DEVICE

[75] Inventor: Roland Brodard, Villeneuve, Switzerland

[73] Assignee: Medicomex S.A., Geneva, Switzerland

[21] Appl. No.: 345,660

[22] PCT Filed: Mar. 26, 1986

[86] PCT No.: PCT/CH86/00040

§ 371 Date: Jan. 12, 1987

§ 102(e) Date: Jan. 12, 1987

[87] PCT Pub. No.: WO87/00760

PCT Pub. Date: Feb. 12, 1987

[30] Foreign Application Priority Data

Apr. 3, 1985 [CH] Switzerland .................. 1438/85

[51] Int. Cl.⁵ .............................................. A61N 1/00
[52] U.S. Cl. ..................................... 128/421; 128/427
[58] Field of Search ................... 128/421, 422, 423 R

[56] References Cited

FOREIGN PATENT DOCUMENTS

| 0087617 | 9/1983 | European Pat. Off. | 128/421 |
| 0165049 | 12/1985 | European Pat. Off. | 128/421 |
| 2123698 | 6/1983 | United Kingdom | 128/421 |
| 2175806 | 12/1986 | United Kingdom | 128/421 |

Primary Examiner—Lee S. Cohen
Assistant Examiner—Scott Getzon
Attorney, Agent, or Firm—Richard Bushnell

[57] ABSTRACT

A stimulating unit (B) equipped with electrodes (34) includes means for generating trains of electrical pulses of different frequencies, and means (2) controlled by a card (6) on which a treatment program is recorded. A programming unit (A) can be separately connected to the stimulating unit (B) by a detachable cable (22); it includes a keyboard (16), a display (17), a printer and means for recording treatment programs on the cards (6) which are subsequently to be introduced into the stimulating unit (B) in order to control it.

The electrodes (34) are applied to the patient during programming, enabling the therapist immediately to check the effect of the programming settings on the patient.

5 Claims, 6 Drawing Sheets

ELECTRICAL NEUROMUSCULAR STIMULATION DEVICE

FIELD OF THE INVENTION

Apparatuses for electrical neuromuscular stimulation have been known for a long time and are used either to prevent muscular atrophy after an accident or operation, or to make certain muscles work in order to strengthen them. Many of these apparatuses use trains of electrical pulses which vary considerably from one apparatus to another. The frequency of the pulses is generally chosen within the approximate range extending from Hz to tens of KHz.

Experimental studies in physiology, carried out in recent years, have demonstrated the fact that the work of muscles is much more complex than had previously been imagined and that, consequently, the devices for electrical neuromuscular stimulation which have been proposed hitherto are actually rather rudimentary and poorly suited to the physiology of the muscles. The data on this subject which are currently to be found scattered throughout the literature show that the muscle tissue is not homogeneous and that it is formed of at least three types of fiber: a first category called slow-acting fibers and two types of fiber which respectively act quickly and very quickly. These three types of muscle fiber cannot be stimulated by the same frequencies of stimulating current; some frequencies are only suitable for the slow fibers and other frequencies for the quick fibers.

Furthermore, other studies have shown that the relatively short treatments applied hitherto are totally inadequate for combating muscular atrophy and ensuring muscle development, for example for athletes. In reality, it is necessary to envisage daily treatments lasting several hours per day, for example up to 5 hours. This presents problems, however, because other studies have shown that long treatments at constant frequencies are likely to produce harmful effects in the muscles, either by damaging the fibers or by modifying the fibers, with the result that, during the treatment, slow fibers are converted to quick fibers or vice-versa, according to the stimulating frequency used. In fact, it has not long been known that the character of the muscle fibers is not fixed. On the contrary, the proportion of the three types of fiber can change according to the work—and hence the excitation—imposed on the muscle. The fibers are capable of converting from one category to another. The frequencies should therefore be appropriately chosen and the different frequencies should be used in a balanced way to stimulate the slow fibers and the quick fibers in a manner which is itself balanced, so as not to introduce subsequent perturbations into the muscle structure.

Other studies have shown, especially with regard to the quick fibers, that it is absolutely essential to observe much longer rest periods than had previously been imagined between the different wave trains of electrical stimulation, in order to ensure that the muscle is not ultimately intoxicated by the chemical substances produced by the muscle work itself. In other words, a sufficient repair time must be allowed between the successive trains of pulses, this time being much longer than had been imagined.

Yet another problem arises because of the length of the treatments required, as we have just seen. For economic reasons, the patient cannot conceivably be asked to undergo daily sessions, lasting several hours, in a hospital or with the physiotherapist, since they would occupy premises, staff, large numbers of expensive apparatuses, etc.; it is therefore advisable to consider having an apparatus for each patient, enabling him to carry out a treatment according to a program tailor-made to suit his particular case. However, an apparatus of this type would of course have to be simplified to the greatest possible extent and be driven by a program recorded on a transfer element, it then being possible for the program to be set up in a hospital or by the therapist on a programming apparatus which would be used to set up the program while it is linked up to a stimulating apparatus connected to the patient, thereby enabling the doctor or therapist to regulate the frequencies, durations, intervals between wave trains, etc. (i.e. the various parameters) in a manner suited to the case, and to keep the maximum intensities below the danger thresholds, this apparatus making it possible, once all the data have thus been brought under the control of the doctor observing the patient, to record on a medium, for example a magnetic card, any program which will thereafter be introduced into the patient's stimulating apparatus, which will subsequently operate autonomously.

During this programming process, the current intensity used for the pulses should obviously be limited so as not to cause damage to the tissues. However, it is also necessary to provide means which ensure that the intensity can only be regulated during the work phase of the pulse trains. In fact, if this regulation is carried out during the formation phase of a pulse train, or during the quenching time of the pulse, or during the rest period between two pulse trains, the therapist no longer has control over the effects of his regulation and this may be dangerous.

These safety means are also operative when the patient himself modifies the intensity of the stimulating current by pressing the buttons 25.

State of the Art

It has already been proposed in French Patent No. 1.213.080 to employ a programming apparatus for recording a treatment program on a medium, and a patient's application apparatus controlled by the program recorded on this medium. It is thus possible, with a single programming apparatus, to have any number of application apparatuses which are each provided with a program suited to the case of the patient to whom this application apparatus is entrusted for home treatment. In the said patent, provision is made for the programming, for a given patient, to take place while the patient is undergoing the treatment by way of a test to guide the programmer.

In German Published patent application DOS 29. 03.392, it is proposed to carry out the stimulation by means of an apparatus controlled by a program which has been recorded beforehand on a medium placed in this apparatus, the program being selected according to the patient's case.

European Published patent application No. 0.087. 617 describes a programming apparatus for recording on a medium a treatment program suited to each patient's case, and a use apparatus into which this medium is introduced and which is controlled by the program.

French Published Patent Application No. 2.528. 709 (derived from U.S. patent application Ser. Nos. 390,026 and 390,027) describes a biological electrical stimulator to be worn by a patient (ambulant treatment), which is controlled by a recording medium consisting of a program card inserted in the stimulator and programmed according to the patient's case. This apparatus is described as analgesic.

None of the apparatuses described in these publications is designed to take account of the conditions referred to above, which must be observed in order to achieve effective muscle development or muscle reeducation without running the risk of damaging the muscle tissues.

The aim of the present invention is to provide a device for electrical neuromuscular stimulation which is designed to satisfy the conditions shown by recent physiological researches to be necessary for ensuring an effective treatment of the muscles without any risk of damaging them. It relates to a device for electrical neuromuscular stimulation in order to cause muscle contractions and muscle exercise or training, comprising at least one autonomous portable stimulating unit controlled by a removable and interchangeable information storage medium programmed beforehand according to the treatment of each patient in question, for supplying trains of electrical stimulating pulses at its output, which is equipped with at least one pair of electrodes to be applied to that part of the patient's body which is to be treated, wherein the stimulating unit comprises means for generating trains of electrical pulses whose characteristics are matched to the slow muscle fibers, and other trains of electrical pulses whose characteristics are matched to the two known types of quick fibers, wherein this stimulating unit comprises means for ensuring, under the control of the program recorded on the removable information storage medium, a muscle treatment which is balanced from the point of view of the frequencies of the stimuli and the durations of the pulse trains, according to the characteristics of the muscles treated and of the patient, and wherein the stimulating unit comprises means, controlled by a microprocessor and capable of being actuated by the patient, for regulating exclusively the intensity of the stimulation within the programmed limits, safety means, incorporated in the same microprocessor, for imposing a preset growth law governing the intensity of the stimulating currents, and for preventing this intensity from increasing outside a plateau period of the muscle contraction work phase, and means for imposing, between the successive pulse trains intended at least for the quick fibers, a sufficient time to ensure elimination of the harmful effects of the work of these fibers, so as to enable a treatment to last several hours without disadvantages.

DESCRIPTION OF THE DRAWINGS

By way of example, the attached drawings show an embodiment of the device forming the subject of the invention.

DESCRIPTION OF THE INVENTION

Figure 1:
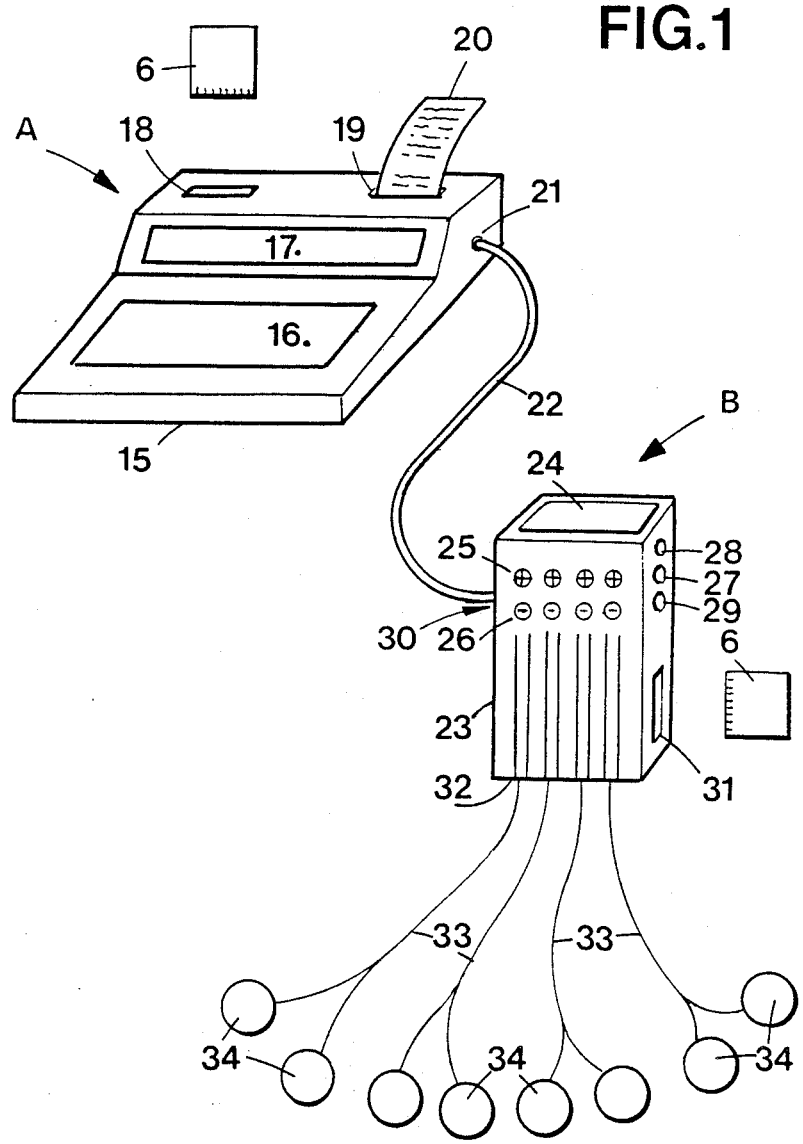
FIG. 1 is a schematic view, in perspective, of the whole of this embodiment, which comprises a programming unit A and a stimulating unit B, linked by a detachable cable.
Figure 2:
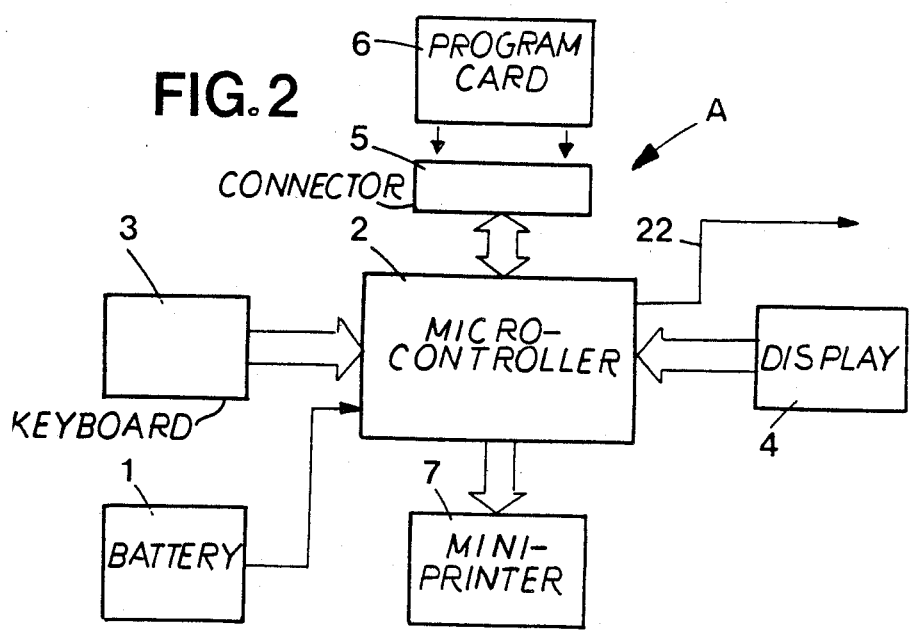
FIG. 2 is a block diagram of the programming unit A of FIG. 1.

The device illustrated in FIG. 1 comprises an autonomous portable programming unit A which consists of a casing 15 containing the constituent mechanical and electronic components corresponding to the block diagram illustrated in FIG. 2, while the outside of the casing provides the operator with the following: a control and data entry keyboard located at 16; an LCD located at 17; an aperture 18 for inserting a program card 6; an aperture 19 for delivering labels 20 formatted by a miniprinter incorporated in the frame; and a connector 21 providing a series interface with a stimulating unit B by means of a detachable cable 22. These labels show in plain language the program which is recorded on the program card 6 introduced at 18.

Figure 3:
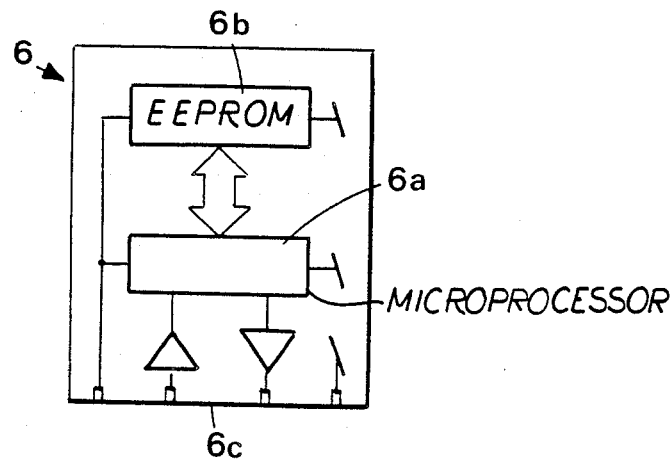
FIG. 3 illustrates, in the form of a block diagram, a program card used with the device according to FIG. 1.

The stimulating unit B is portable and autonomous; it is produced according to a general design in the style of a "walkman". Its casing 23 contains the constituent mechanical and electronic components corresponding to the block diagram in FIG. 3, while the outside of the said casing provides the user with the following: an LCD 24 for monitoring the functions (duration of the treatment, sequence in progress, charge condition of the batteries, and bar charts indicating the intensity of the stimulating signal at each output); a control 25 for increasing or 26 for decreasing the intensity of the stimulating signal at each output; a control 27 for starting the treatment; a control 28 for momentarily interrupting the said treatment; a control 29 for momentarily suppressing the rest period; a connector 30 for connecting the detachable cable 22 which provides a series interface with the programming unit A; an aperture 31 for inserting the program card 6; and connectors 32 for connecting the cables 33 of each pair of electrodes 34.

In FIGS. 1 and 2, A is a programming unit. It includes a rechargeable battery 1 supplying a microcontroller 2, comprising a microprocessor, into which a ROM (read-only memory) and a RAM (random access memory) are directly integrated. This microcontroller makes it possible to record, store and manage all the parameters for initiating a treatment and controlling its progress, in accordance with a previously stored program. The main initiating parameters are as follows:

The shape of the pulse, i.e. the variation of its amplitude as a function of its duration.

The amplitude of the pulse.

The duration of the pulse.

The pulse recurrence frequency.

The duration of a pulse train.

The duration of the interval separating two consecutive pulse trains.

The formation time or slope of a pulse train.

The microcontroller 2 is linked to the keyboard 3 located at 16 (FIG. 1), which enables the operator to select the said parameters for initiating a treatment and controlling its progress, and to determine the value assigned to each of the parameters selected, and then to introduce these data into the microcontroller, where they will be managed in accordance with the preset program.

The keyboard 3 and the microcontroller 2 are linked to the alphanumeric display 4, of the LCD (liquid crystal display) type, which allows operator-machine dialog and makes it possible to monitor the data introduced. This display is located at 17 in FIG. 1.

The microcontroller is also linked to a connector 5, which is the means of connection to a removable data storage medium 6 (FIGS. 1 and 3), which is represented in this case by a plastic card having the same format as a standard credit card, for example, and which contains (FIG. 3) a microprocessor 6a linked to an EEPROM (electrically-erasable programmable read-only memory) 6b and to a connector 6c. The said medium 6 is distinguished by its non-volatile storage and by its ability to write and electrically read the stored data, as will be seen below.

The microcontroller 2 is also linked to a miniprinter 7 making it possible to format, on a self-adhesive label 20, the data which characterize the prescribed programmed treatment of neuromuscular stimulation, recorded on the card 6 by means of the keyboard 3 (16), and the patient to whom it applies. The said data can be introduced via the keyboard 3 and/or can originate from a treatment management program previously stored in the microcontroller 2. The self-adhesive label is then attached to the programmable data storage medium or card, thereby enabling its contents to be identified in plain language.

Finally, by means of the connector and a cable 22 (FIG. 1), the microcontroller 2 is provided with a series interface enabling the autonomous programming unit A, illustrated in FIGS. 1 and 2, to operate on line with a neuromuscular stimulating unit B.

The stimulating unit B (FIGS. 1 and 4) includes a battery 8, preferably a removable block of rechargeable nickel-cadmium batteries, supplying a microcontroller 9. This microcontroller is linked by means of the connector 10 to the removable data storage medium, which is represented in this case by the programmable card 6 already described above and illustrated in FIGS. 1 and 3.

The microcontroller 9 of the stimulating unit B and the microcontroller 6a of the removable data storage medium 6 thus have the ability to communicate interactively with one another, thereby making it possible not only to manage all the data necessary for the correct execution of a treatment program, but also to operate the programming unit and the stimulator online when these two units of the device are linked to one another by the series interface 22 (FIG. 1).

On-line operation is understood as meaning that all the parameters processed by the programming unit can be tested in real time on the patient, in the form in which they are introduced into and returned by the stimulator, and in the form in which they have to be integrated into the program which they partially define. At the same time, each parameter is stored on the removable data storage medium 6. It is consequently necessary only to interrupt the on-line operation for the said removable data storage medium to be loaded with the program tested in real time on the patient.

The system which has now been described makes it possible to load the program card 6 in several ways:

With the program card inserted in the stimulator, it is loaded at the same time as the treatment program is set up by means of the programming unit and at the same time as its on-line test on the patient by means of the stimulator.

With the program card 6 inserted in the programming unit A at 18, it can then be loaded by means of the said programming unit in the absence of the stimulator B, but without the set program being able to be tested simultaneously on the patient.

A program card 6 inserted in the programming unit A can be read and stored and subsequently replaced at 18 with another card; it can then be copied onto the latter, thus making it possible to duplicate a program on one or more programmable cards.

The interactive communication between the microcontrollers of the stimulator and of the removable data storage card enables information relating to the real-time progress of the programmed treatment to be written and stored on the said card.

Thus, by way of example, provision can be made to record the real time for which the patient applies his prescribed treatment. The real-time data thus returned by the stimulator and stored on the removable data storage card can be interpreted and read back by means of the programming unit. The therapist thus has at his disposal a valuable means of checking that the application of the prescribed treatment is being observed.

Figure 4:
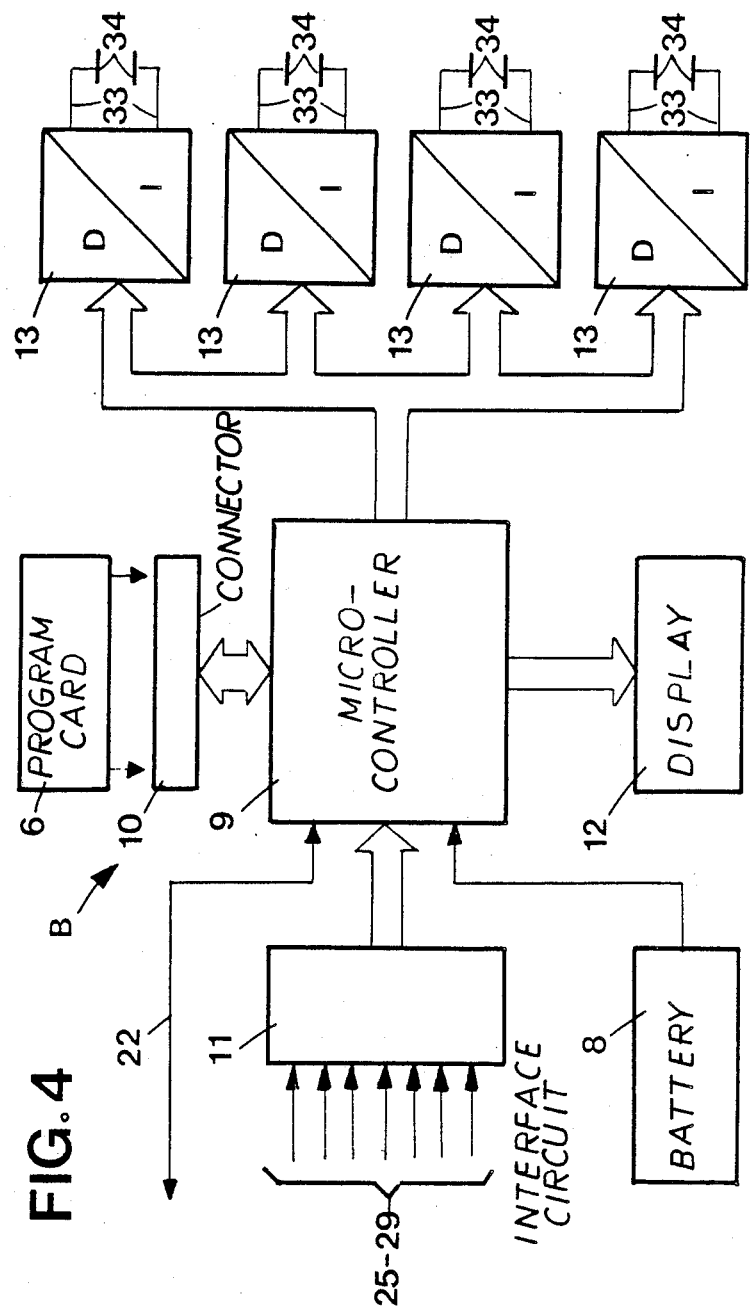
FIG. 4 is a block diagram of the stimulating unit B of FIG. 1.

With reference to FIG. 4, the microcontroller 9 is also linked, by means of an input interface circuit 11, to the manual control devices on the stimulator, which are accessible only to the patient and which, in the example, amount to the following:

A control 28 (on/off) for starting and stopping the stimulator.

A control 29 for momentarily suppressing the rest period between two consecutive contraction periods in order to facilitate regulation of the magnitude of the muscle contraction force generated by the stimulation.

A control 27 for starting the treatment, momentarily interrupting the treatment or resuming the treatment after an interruption, or else starting a nonautomatic sequence.

A control for regulating the amplitude of the pulse signal delivered at each of the outputs; the buttons 25 correspond to increases in amplitude and the buttons 26 to decreases. These switches are active while being pressed.

The microcontroller 9 is also linked to an alphanumeric display 12 of the LCD (liquid crystal display) type, shown at 24 in FIG. 1, which indicates the residual treatment time left to run, the identification of the sequence which is in progress, the level of charge in the batteries and, by means of bar charts, the amplitude in analog form of the pulse signal delivered at each of the outputs.

Finally, the microcontroller 9 is linked to each of the output stages 13. Each of the output stages, which are galvanically insulated from one another, uses a digital-to-pulse converter to convert the programmed digital signal generated by the microcontroller into a corresponding pulse signal delivered through the said output. This signal is applied to the patient transcutaneously by means of the cables 33 and the pairs of surface electrodes 34, there being one pair per output.

Figure 5:
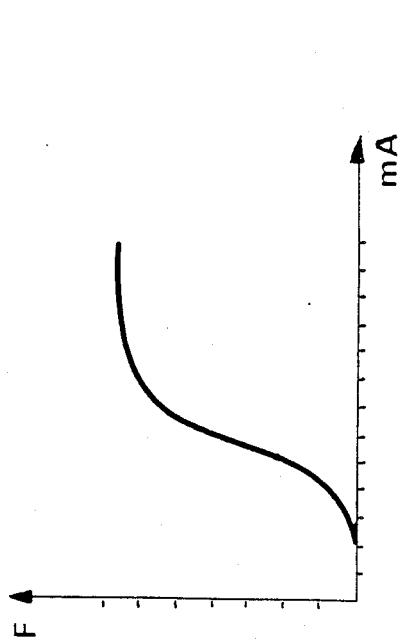
FIG. 5 illustrates the shape of the curve representing the variation in the magnitude of the muscle contraction force as a function of the increase in the intensity of the pulse signal for stimulating the muscle.

The increase in the magnitude of the force delivered by the muscle contraction as a function of the increase in the intensity of the stimulating pulse signal is neither linear nor logarithmic. It gives a characteristic curve peculiar to the reaction of the muscle through which the stimulating current is passed, as illustrated in FIG. 5. Consequently, the customary means are unable to regulate the muscle contraction force in a manner which is at one and the same time convenient, gradual, fine and precise; these means are generally represented by linear or logarithmic potentiometers. A considerable advance is to allocate to the microcontroller 2 the function of integral control over the variation in the intensity of the pulse signal delivered at the output, as regards both the determination of its shape and its mode of application. By appropriately programming the said microcontroller, it is possible to adapt the variation in the intensity of the output pulse signal as a function of the time t in such a way that the corresponding variation in the magnitude of the contraction force F satisfies the optimum regulation conditions desired to ensure the patient's safety (FIG. 5).

The said programming also defines the mode of application by virtue of the microcontroller 9, in the sense that it only allows the contraction force to increase during a work period (contraction force at its plateau) and, conversely, prohibits it from increasing during the formation time of the said force, as well as in the absence of stimulation, for example during a rest period between two consecutive contractions.

Figure 6:
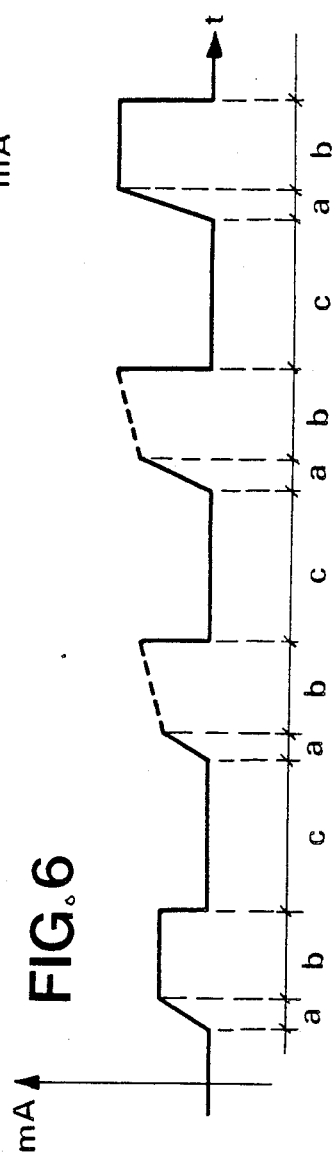
FIG. 6 is a schematic diagram of the amplitude of the pulse signal delivered at the output of the device according to FIG. 1, as a function of time, showing the zones in which an increase in the contraction force (during programming) is permissible and those in which an increase must conversely be prohibited by the device, as explained below.

In FIG. 6, which represents the amplitude, in milliamperes, of the electrical stimulating pulses as a function of the time t, the following are denoted by a, b and c:

| | |
|---|---|
| a | = formation time of the pulse |
| b | = nominal plateau intensity |
| a + b | = duration of the pulse train = period of muscle work |
| c | = rest period |

Regulation of the intensity is only permitted during period b since it is only during this period that the programming unit can observe the effect of this regulation on the patient. The microcontroller 9 prohibits (prevents) regulation from taking place during periods a and c in order to ensure the patient's safety. This is an extremely important safety measure because any unexpected and unmonitored increase in the muscle contraction force in vivo, in real time, can have harmful and dangerous consequences for the muscle.

This program for regulating the contraction force is driven by the transitory-action manual control devices 25 and 26. When the operator keeps the first control in the active position, the contraction force gradually increases in accordance with the programmed variation law, while pressing the second control causes this same force to decrease.

The framework of the present invention does not include the method for correctly determining the various optimum parameters for initiating a treatment and controlling its progress. This is because these parameters vary greatly with the particular activity scheme which the therapist wants to impose on the muscles in accordance with his specific therapeutic objectives pertaining to each case and each patient, and also with the present physiology of the muscle.

Figure 7A:
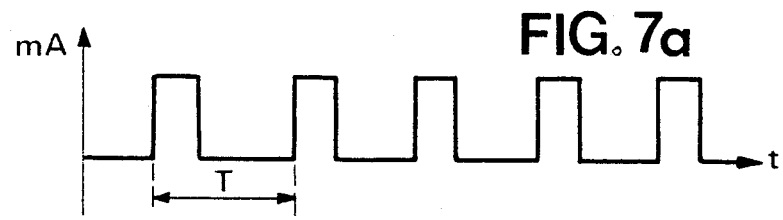
FIGS. 7a, 7b and 7c schematically illustrate conventional pulsed waveforms which can be programmed as desired.
Figure 7B:
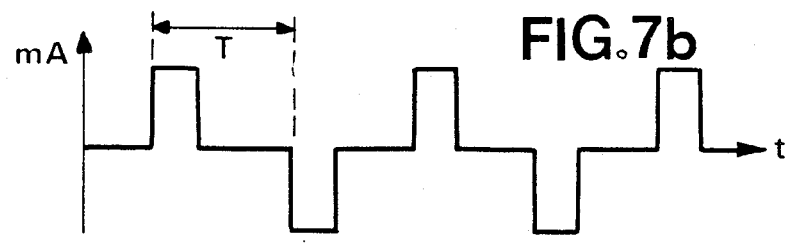
Figure 7C:
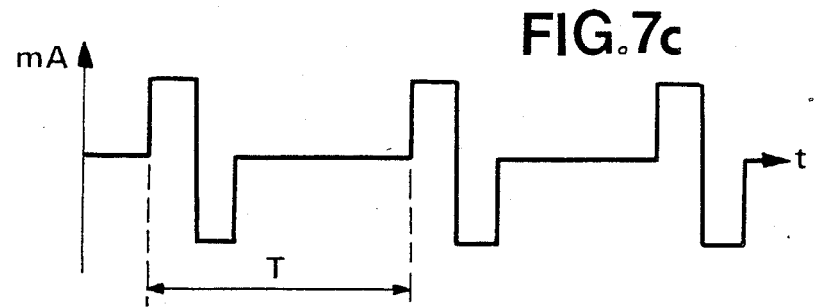
Figure 8A:
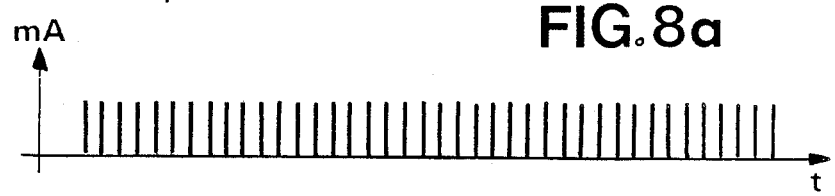
FIGS. 8a and 8b schematically show the application of the pulses in continuous mode and in intermittent mode (pulse trains).
Figure 8B:
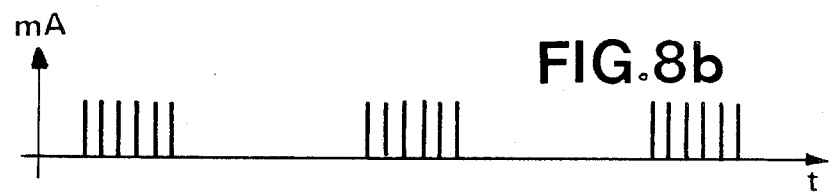
Figure 9A:
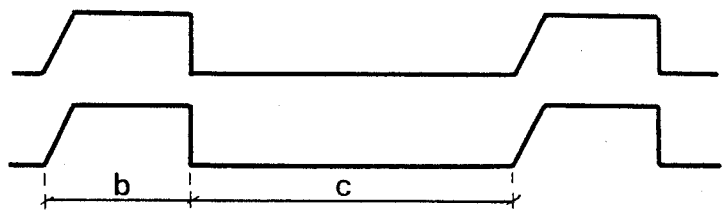
FIGS. 9a and 9b illustrate the absolute work mode of the outputs and the reciprocity time in alternate mode.
Figure 9B:
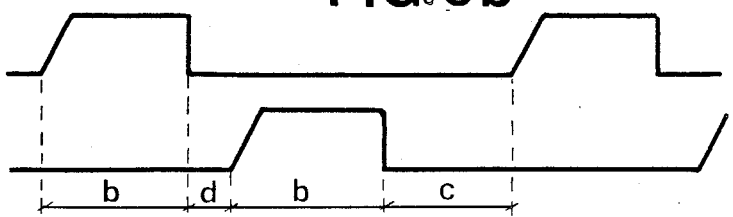

By way of example, however, the programmable parameters for initiating a treatment and controlling its progress are indicated together with the range of programmable values which can usually be assigned thereto:

Duration of a treatment session:
 expressed in terms of time: from 1 minute to 10 hours, resolution 1 minute
 expressed in terms of the number of work cycles: from 1 to 100.
Number of sequences (i.e. time for which the programmed initiating parameters remain constant) within a treatment session: from 1 to 10.
Then within each sequence:
Duration of the sequence:
 less than or equal to the duration of the treatment.
Pulse or stimulus (square waveform of period T):
 one-phase type (unidirectional), FIG. 7a
 two-phase type with symmetrical alternation, FIG. 7b
 two-phase type with direct symmetry, FIG. 7c.
Duration of the pulse: from 0.01 to 1.0 millisecond, resolution 10 μs.
Pulse recurrence frequency: from 1 to 200 pulses per second.
Mode of application of the pulses:
 continuous permanent mode, FIG. 8a
 cyclic intermittent mode (succession of work and rest periods), FIG. 8b.
Absolute work mode of the outputs:
 synchronous: all the outputs work simultaneously, FIG. 9a
 alternate: half the available outputs work in alternation with the other half, FIG. 9b
 b = work period
 c = rest period
 d = reciprocity period (shift between the alternate pulses at the outputs).
Control of the delivery of the pulses at the outputs:
 automatic, in accordance with the programming of the mode of application of the pulses
 by remote control, which initiates a phase of the programmed mode of application.

Figure 10:
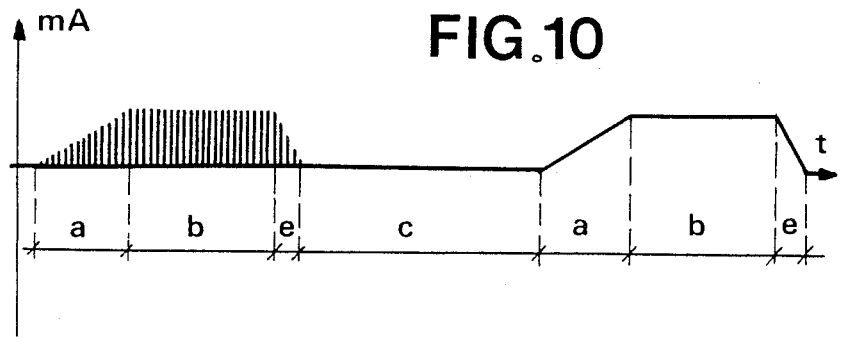
FIG. 10 is a diagram showing the duration of the work period, its formation time and quenching time, as well as the duration of the rest period.

FIG. 10 represents the intensity in mA of the excitation as a function of time. The periods a, b and c are the same as in FIG. 6. e denotes the quenching time of a pulse train.

The following are possible in this case:
Duration of the work period (a+b+e) = contraction = 1 to 60 seconds, resolution 1 second.
Formation time (a) of the work period: from 1 to 20 seconds, resolution 1 second.
Quenching time (e) of the work period: from 1 to 20 seconds, resolution 1 second.
Reciprocity time (d) in alternate mode (FIG. 9b): from 10 to 1000 milliseconds, resolution 10 ms.
Duration of the rest period (c) (muscle relaxation): from 1 to 200 seconds, resolution 1 second.
Switching from one sequence to the other:
 automatic
 manual.
The device described has the following advantages:

It is possible to have a series of program cards, such as 6 corresponding to various standard programs, and to use them as an individual programming base, modifying their program by means of the keyboard in order to adapt them to each particular patient.

The programming unit A can also be used by the therapist to consult the information cards by introducing them at 18 and reading their contents at 17.

The means for generating pulse trains in the stimulator include the means for bringing the manual control for regulating the intensity of the signal delivered at an output under the control of the microcontroller 9. By appropriately programming the said microcontroller, it is then possible automatically to adapt the variation in the intensity of the said signal as a function of time in such a way that the corresponding variation in the magnitude of the muscle contraction force caused by the said signal satisfies the optimum conditions permitting convenient, gradual, fine and precise regulation.

The means for controlling the manual control of the regulation of the intensity of the pulse signal delivered at an output include the means for only allowing the said signal, and hence the muscle contraction force, to increase during a work period (contraction force at its plateau) and for prohibiting it from increasing during a formation period and in the absence of stimulation, for example during a rest period between two consecutive contractions.

The stimulator's generating means include means for controlling the correct application and execution of the treatment by the patient and for writing the results of the treatment into the said storage means.

The programming means include means for interpreting, displaying on a screen, formatting and printing out, according to a program and in plain language, not only the data entered via the keyboard allocated to the said programming means, but also the data stored by the said storage means detachably connected to the said programming means.

The programming means can be detachably connected to the stimulator's generating means by a series interface which ensures on-line operation of the said programming means with the said generating means, thus making it possible to adjust the excitation parameters as a direct function of the immediate reactions of the patient to the stimulation caused.

It is possible to produce electrical neuromuscular stimulation controlled by a free program determined by the therapist in order to define sequential schemes of muscle activity ensuring that the treatment is optimally adapted to:

each type of patient in question;

the therapeutic objectives set according to each specific case;

the present physiology of the muscle;

the exclusion of sensitive and/or harmful physiological side-effects. .

As the treatment is programmed, it is possible for the patient to carry out the application of the treatment autonomously, at home or in a hospital.

In the interest of total safety, access to the programmable parameters and to the setting-up of the treatment program is strictly reserved for the therapist alone, to the exclusion of the patient, who may only alter the manual regulation of the intensity of the pulse signal delivered at the output, within the limits fixed by the program.

As any program set up for a given treatment is stored in a removable, non-volatile and transportable manner, the said program can be faithfully reproduced at any time and in any place by means of the said stimulating device, without the need for reprogramming.

As the said programs are stored in a removable, non-volatile and transportable manner, they can be interchanged instantly, without any difficulty at all, in order to permit a variety of preprogrammed treatments.

On the same physical medium, the said program carries an identification of its specific characteristics in plain language, eliminating any confusion as regards the contents of the said program and as regards the patient.

What is claimed is:

1. A device for electrical neuromuscular simulation in order to cause muscle contractions and muscle exercise or training, comprising at least one autonomous portable stimulating unit (B) controlled by a removable and interchangeable information storage medium (6) programmed beforehand by a therapist by means of a programming unit (A) according to the treatment of a patient in question, for supplying trains of electrical stimulating pulses at its output, which is equipped with at least one pair of electrodes (34) to be applied to that part of the patient's body which is to be treated wherein the stimulating unit (B) comprises means for generating trains of electrical pulses whose characteristics are matched to the slow muscle fibers of the patient's body, and other trains of electrical pulses whose characteristics are matched to the two known types of quick fibers of the patient's body, wherein said stimulating unit comprises program-actuated means (9) for carrying out, under the control of a sequential program recorded on the removable information storage medium (6), a muscle treatment by said trains of electrical pulses; means for regulating the frequency and the durations of the pulses of said trains of electrical pulses, according to the characteristics of the muscles treated and of the patient, and wherein the stimulating unit (B) comprises intensity regulating means, controlled by a microprocessor and capable of being actuated by the patient, for regulating the intensity of the stimulation within predetermined programmed limits; safety means, incorporated in the same microprocessor, for maintaining the variation of the muscular contraction force to he substantially linear as a function of time, and for preventing an increase of the current intensity of the stimulating pulses to occur outside a predetermined plateau period (b) of the muscle contraction work phase, and for imposing, between at least those pulse trains intended for the quick fibers, a sufficient delay time (c) to avoid any harmful effects to said both types of fibers, so as to enable a treatment to last several hours without such harmful effects.

2. The device as claimed in claim 1, wherein the stimulating unit includes means for recording, on the information storage medium (6) which controls said stimulating unit during the treatment, parameters relating to the nature, duration and number of the treatments actually carried out upon the patient, so that the therapist can subsequently check whether the treatment has been carried out in accordance with his instructions.

3. The device as claimed in claim 2, wherein the regulating means provided on the stimulating unit, which are available to the patient, are restricted to manual regulation of the intensity of the output pulses within the limits fixed by the program recorded on the information storage medium.

4. The device as claimed in claim 1, wherein the programming unit (A) is intended for recording programs on information storage media intended for the stimulating unit (B), means being provided for detachably interconnecting this programming unit with the stimulating unit, which device includes means (22) so that, during programming, with the stimulating unit (B) interconnected with the programming unit (A), the patient is himself connected to the programming unit (A), via the stimulating unit (B), and receives the pulses corresponding to a present setting, so that the therapist immediately observes the effect on the patient of every change in the setting.

5. The device as claimed in claim 4, wherein the programming unit (A) comprises a programming keyboard, display means controlled by the keyboard, a printer, a microprocessor, a memory and means for detachably interconnecting the information storage medium (6) so that, in a first stage, standard programs and/or therapeutic information carried on a first said removable and interchangeable information storage medium (6), called a reference medium and forming part of a library, can be read, stored and interpreted, and so that, in a second stage, after the connection of a second said removable and interchangable information storage medium (6) for controlling the operation of the stimulating unit (B), the therapist can compose and record, on the said information storage medium, a program resulting from the information provided by the reference medium and/or a program independent thereof, check its accuracy in the course of programming and obtain a version, written in plain language, of the program recorded on the information storage medium.

* * * * *

UNITED STATES PATENT AND TRADEMARK OFFICE
CERTIFICATE OF CORRECTION

PATENT NO. : 4,919,139
DATED : April 24, 1990
INVENTOR(S) : Roland Brodard

It is certified that error appears in the above-identified patent and that said Letters Patent is hereby corrected as shown below:

Title page:

Please make the following correction:

SERIAL NO. "345,660"

should be-- 945,660--

Signed and Sealed this

Thirtieth Day of July, 1991

Attest:

HARRY F. MANBECK, JR.

*Attesting Officer*  *Commissioner of Patents and Trademarks*